(12) United States Patent
Tabata et al.

(10) Patent No.: US 6,511,439 B1
(45) Date of Patent: Jan. 28, 2003

(54) BLOOD-COLLECTING DEVICE

(75) Inventors: Yasushi Tabata, Kanagawa (JP); Yasuhiro Ishiguro, Yamanashi (JP); Yukio Koshimura, Yamanashi (JP); Nobuo Yoshino, Yamanashi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1 day.

(21) Appl. No.: 09/727,681

(22) Filed: Dec. 4, 2000

(30) Foreign Application Priority Data

| Dec. 7, 1999 | (JP) | 11-347842 |
| Dec. 7, 1999 | (JP) | 11-347843 |
| Dec. 21, 1999 | (JP) | 11-363495 |

(51) Int. Cl.$^7$ .............................. A61B 5/00
(52) U.S. Cl. ............ 600/573; 600/576; 600/578; 600/584; 604/6.07
(58) Field of Search .............. 600/573, 576, 600/578, 584, 577; 604/4.01, 6.05, 6.06, 6.07, 269

(56) References Cited

U.S. PATENT DOCUMENTS

| 3,886,928 A |   | 6/1975 | Sarstedt |
| 4,215,701 A |   | 8/1980 | Raitto |
| 4,326,541 A |   | 4/1982 | Eckels |
| 4,361,155 A | * | 11/1982 | Anastasio .................. 600/576 |
| 4,448,206 A |   | 5/1984 | Martell |
| 4,595,021 A | * | 6/1986 | Shimizu et al. ............. 600/578 |
| 4,687,000 A | * | 8/1987 | Eisenhardt et al. ......... 600/573 |
| 5,093,263 A | * | 3/1992 | Marlar et al. ............... 422/102 |
| 5,807,344 A | * | 9/1998 | Iwasaki ...................... 600/576 |
| 6,126,643 A | * | 10/2000 | Vaillancouert .............. 600/576 |
| 6,340,675 B1 | * | 1/2002 | Mancilla et al. .............. 514/56 |

* cited by examiner

*Primary Examiner*—Henry Bennett
*Assistant Examiner*—Kathryn Ferko
(74) *Attorney, Agent, or Firm*—Burns, Doane, Swecker & Mathis, LLP

(57) ABSTRACT

A blood-collecting device comprises an outer cylinder, a gasket slidable in the outer cylinder, and a plunger for the moving operation of the gasket. A ventilatable filter member is mounted on the tip end part of a hole formed in the gasket. The hole communicated with the outside via the hole of the plunger and the internal space. An anti-coagulation agent supply piece with an anti-coagulation agent such as a heparin supported on one side or both sides of a plate-like supporting member is provided in a space surrounded by the outer cylinder and the gasket. The tip end side of the anti-coagulation agent supply piece having a shape tapered toward the blood inlet opening, and the anti-coagulation agent supply piece maintains its posture by linear contact of a pair of sides facing with each other with the inner surface of the outer cylinder.

13 Claims, 8 Drawing Sheets

BLOOD-COLLECTING DEVICE

BACKGROUND OF THE INVENTION

1. Field of the Invention

The present invention relates to a blood-collecting device to be used for collecting the blood, in particular, it relates to an arterial blood-collecting device for collecting the arterial blood.

2. Description of the Related Art

The arterial blood is collected for analyzing and measuring the dissolved oxygen amount, or the like in the blood. Unlike collection of the venous blood, an arterial blood-collecting device used therefor has a configuration wherein the blood is introduced into the blood-collecting device according to the blood pressure in the artery.

In this case, since the air in the syringe should be discharged to the outside as the blood is introduced into the syringe of the blood-collecting device by the blood pressure, the inside and the outside of the syringe can be ventilated via a filter member.

Furthermore, since the accurate analysis is disabled in the case the collected blood is coagulated, an anti-coagulation agent such as heparin is provided in the syringe of the arterial blood-collecting device.

In this case, since the heparin is stored in the syringe in the freeze-dried state, there are the following disadvantages.

Firstly, the freeze-dried heparin can easily absorbs moisture so as to be liquidized due to the generated deliquescence phenomenon. Therefore, problems arise in that:

existence of the heparin in the syringe cannot be confirmed;

in the case where the liquidized heparin flows out so as to be adhered and absorbed by the filter member, the filter is choked so as to disable or hinder the gas exhaustion according to the introduction of the blood; and since the liquidized heparin is mixed into the collected blood so as to dilute the blood, the accurate analysis and measurement are prevented.

Secondly, bubbles are generated at the time of introducing the blood so as to be mixed in the collected blood. Therefore, the measurement values such as the dissolved oxygen amount are affected so that the accurate analysis and measurement are prevented.

Thirdly, much labor is required because a heparin solution needs to be processed by freeze-drying.

Here, as mentioned above, since the space with the heparin stored can be ventilated with the outside via the filter member, in order to prevent the first problem of the moisture absorption of the heparin, the entirety of the arterial blood-collecting device should be wrapped in a special wrapping material having the excellent vapor barrier property, such as a wrapping material comprising a laminated film having an aluminum thin layer.

Therefore, it causes the cost rise as well as since the inside of the wrapping material is invisible, it is disadvantages in terms of the quality control. Besides, there is a problem of difficulty in the disposal of the wrapping material.

Moreover, there is a problem of the need of much labor in the production of the blood-collecting device because a heparin solution needs to be processed by freeze-drying.

SUMMARY OF THE INVENTION

An object of the invention is to provide a blood-collecting device with the excellent solubility and mixing property of an anti-coagulation agent with respect to the blood, without the need of a freeze-drying process of an anti-coagulation agent, capable of eliminating or reducing (alleviating) a moisture prevention measure and restraining mixture of bubbles into the collected blood, and further, with a good production efficiency.

The object can be achieved by the below-mentioned blood-collecting devices according to the invention.

According to a first aspect of the invention, the object of the invention can be achieved by a blood-collecting device comprising an outer cylinder having a blood inlet opening, a gasket slidable in the outer cylinder, a plunger for the moving operation of the gasket, and an anti-coagulation agent supply piece with an anti-coagulation agent supported on at least one side of a plate-like supporting member, provided in a space surrounded by the outer cylinder and the gasket.

It is preferable that the anti-coagulation agent supply piece has a shape tapered toward the blood inlet opening.

According to a second aspect of the invention comprising the blood-collecting device of the first aspect, it is preferable that the tip end of the tapered shape is pointed.

According to a third aspect of the invention comprising the blood-collecting device of the first or second aspect, it is preferable that the tip end of the tapered shape is disposed in the blood inlet opening.

According to a fourth aspect of the invention comprising the blood-collecting device of the first or third aspect, it is preferable that the anti-coagulation agent supply piece maintains its posture by linear contact of the rim part with the inner surface of the outer cylinder.

According to a fifth aspect of the invention, the object of the invention can be achieved by a blood-collecting device comprising an outer cylinder having a blood inlet opening, a gasket slidable in the outer cylinder, a plunger for the moving operation of the gasket, and an anti-coagulation agent supply piece with an anti-coagulation agent supported on at least one side of a plate-like supporting member, provided in a space surrounded by the outer cylinder and the gasket, wherein the anti-coagulation agent supply piece maintains its posture by linear contact of the rim part with the inner surface of the outer cylinder.

According to a sixth aspect of the invention, the object of the invention can be achieved by a blood-collecting device comprising an outer cylinder having a blood inlet opening, a gasket slidable in the outer cylinder, a plunger for the moving operation of the gasket, and an anti-coagulation agent supply piece with an anti-coagulation agent supported on at least one side of a plate-like supporting member, provided in a space surrounded by the outer cylinder and the gasket, wherein the anti-coagulation agent supply piece maintains its posture by linear contact of a pair of rim parts facing with each other with the inner surface of the outer cylinder.

According to a seventh aspect of the invention comprising the blood-collecting device of the sixth aspect, it is preferable that the lengths of the pair of the rim parts are substantially equal.

According to an eighth aspect of the invention comprising the blood-collecting device of the first or seventh aspect, it is preferable that the anti-coagulation agent supply piece has a polygonal shape.

According to a ninth aspect of the invention comprising the blood-collecting device of the first or eighth aspect, it is preferable that the plate-like supporting member is made of a material insoluble with respect to the blood.

According to a tenth aspect of the invention comprising the blood-collecting device of the first or ninth aspect, it is preferable that the plate-like supporting member is made of a non-porous material.

According to an eleventh aspect of the invention comprising the blood-collecting device of the first or tenth aspect, it is preferable that minute ruggedness is formed on the surface of the plate-like supporting member in contact with the anti-coagulation agent.

According to a twelfth aspect of the invention comprising the blood-collecting device of the first or eleventh aspect, it is preferable that the anti-coagulation agent is supported by applying a solution of the anti-coagulation agent on the surface of the plate-like supporting member, and drying at an ordinary temperature or higher.

According to a thirteenth aspect of the invention comprising the blood-collecting device of the first or twelfth aspect, it is preferable that the anti-coagulation agent supply piece is disposed in a direction substantially parallel with the longitudinal direction of the outer cylinder.

According to a fourteenth aspect of the invention comprising the blood-collecting device of the first or thirteenth aspect, it is preferable that a ventilation part is formed in the gasket and the plunger.

According to a fifteenth aspect of the invention comprising the blood-collecting device of the fourteenth aspect, it is preferable that a gas permeable filter member not allowing permeation of a liquid is provided in the gasket.

According to a sixteenth aspect of the invention comprising the blood-collecting device of the first or fifteenth aspect, it is preferable that the anti-coagulation agent is a heparin.

The blood-collecting device according to the first or sixteenth aspect is suitable for collecting the arterial blood.

DETAILED DESCRIPTION OF THE PREFERRED EMBODIMENTS

Hereinafter, a blood-collecting device according to the invention will be explained in detail based on the preferable embodiments shown in the accompanied drawings.

Figure 1:
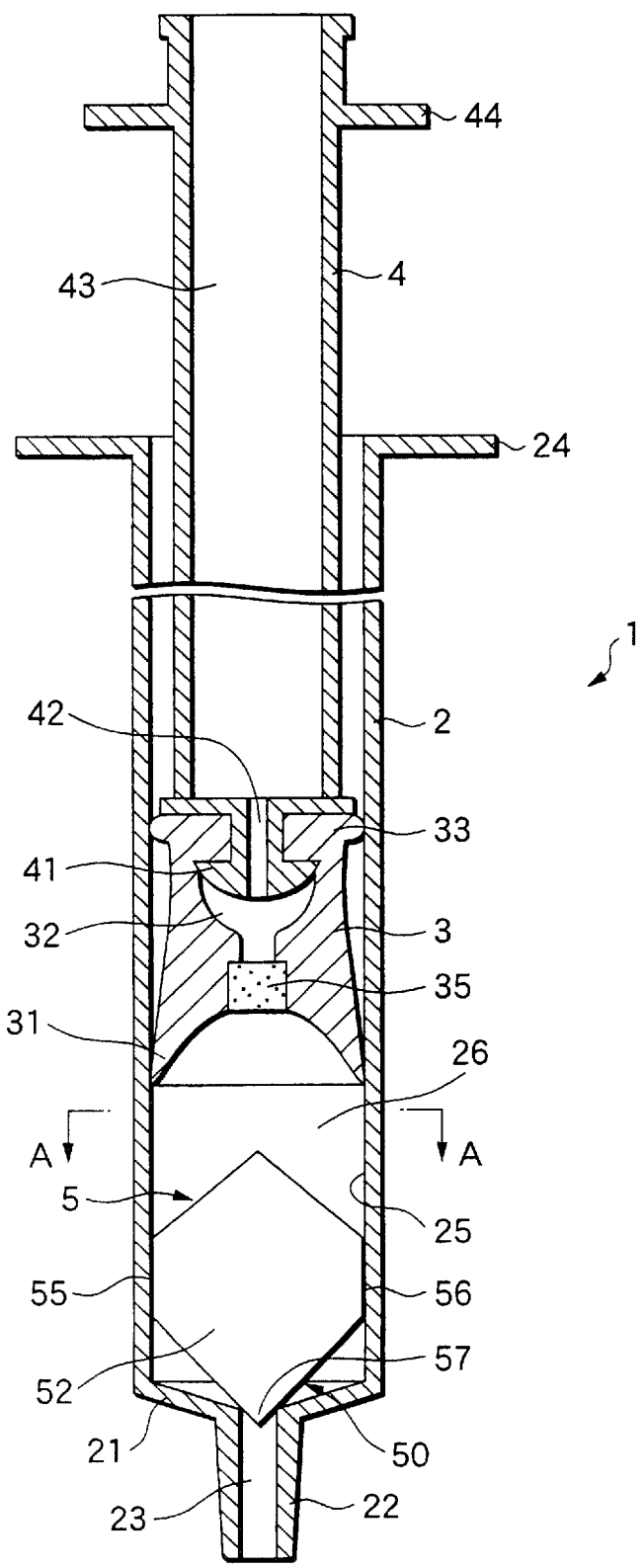
FIG. 1 is a vertical cross-sectional view of an embodiment of a blood-collecting device according to the invention.
Figure 2:
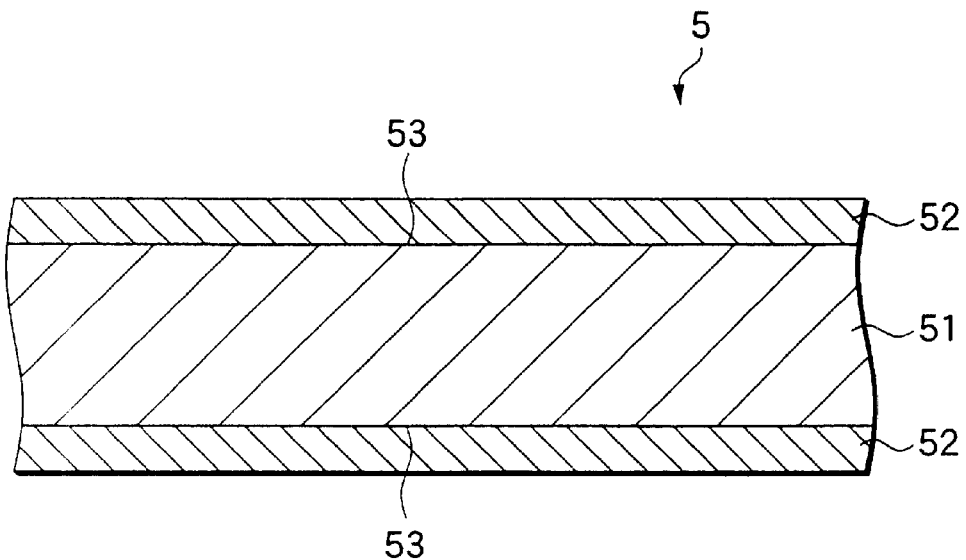
FIG. 2 is a cross-sectional view of a configuration of an anti-coagulation agent supply piece.
Figure 3:
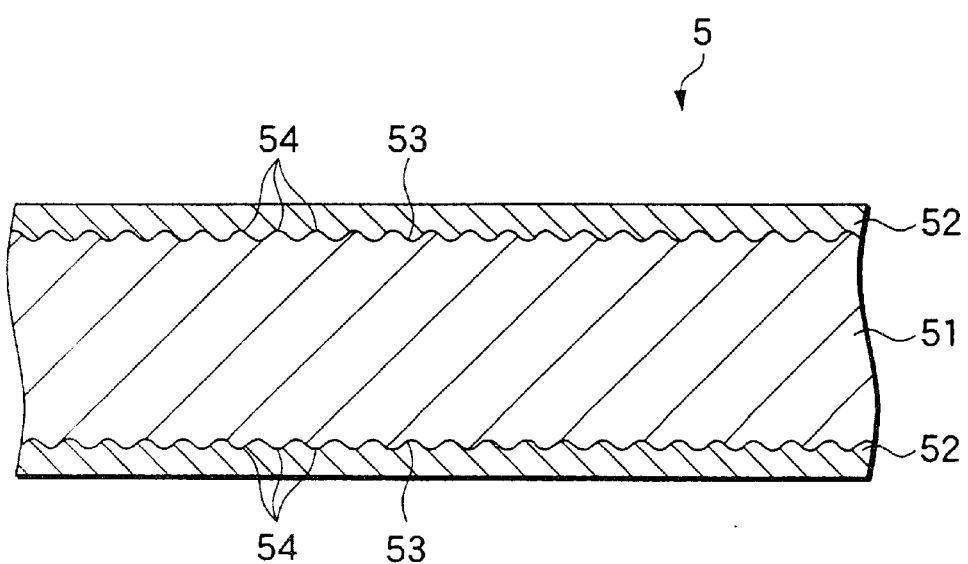
FIG. 3 is a cross-sectional view of a configuration of an anti-coagulation agent supply piece.
Figure 4:
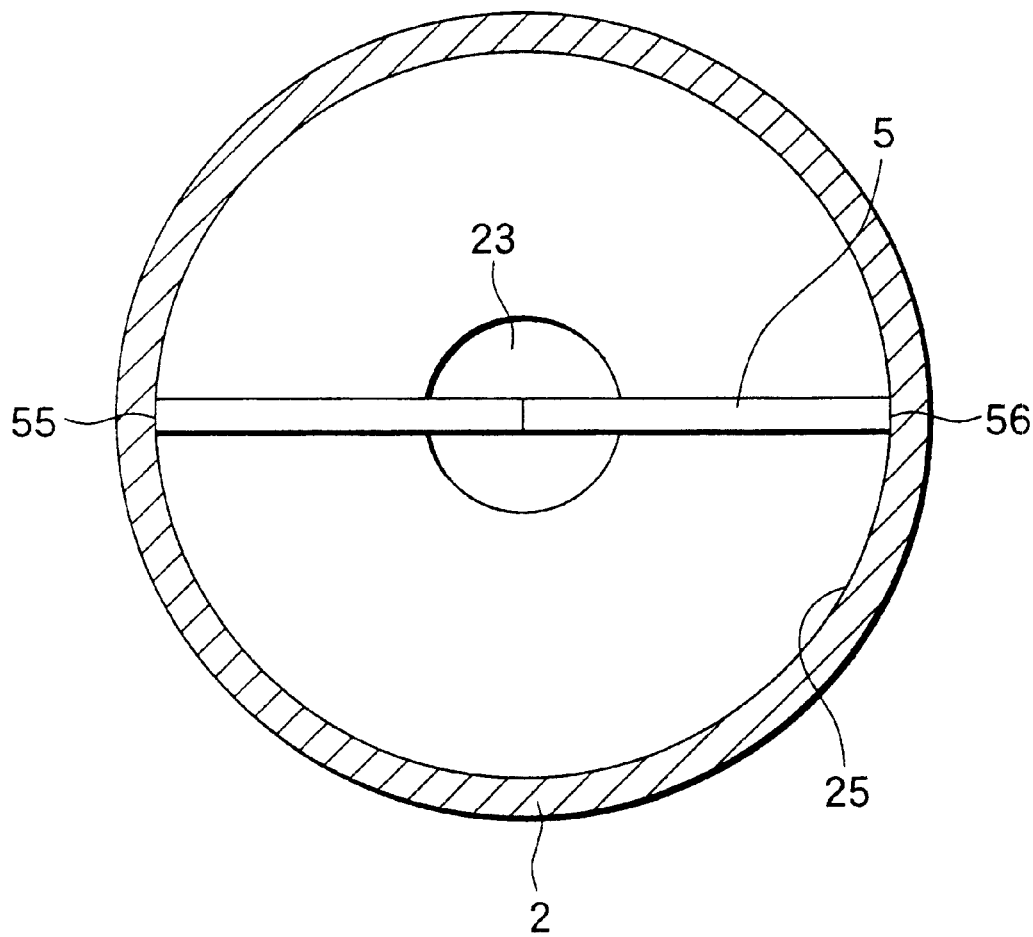
FIG. 4 is a cross-sectional view taken on the line A—A of FIG. 1.

FIG. 1 is a vertical cross-sectional view showing an embodiment of a blood-collecting device of the invention. FIGS. 2 and 3 are cross-sectional views each showing a configuration example of an anti-coagulation agent supply piece. FIG. 4 is a cross-sectional view taken on the line A—A of FIG. 1. For the convenience of explanation, the upper side in FIG. 1 is referred to as the "base end", and the lower side as the "tip end".

The blood-collecting device 1 of this embodiment, which is a blood-collecting device for collecting the arterial blood, comprises an outer cylinder (syringe) 2, a gasket 3 slidable in the outer cylinder 2, and a plunger 4 for the moving operation of the gasket 3.

The outer cylinder 2 comprises a cylindrical member having a bottom part, with a narrow diameter part 22 having a diameter narrower than the body part of the outer cylinder 2 formed integrally in the center part of the bottom part 21. A hub of a needle pipe (not illustrated) for collecting the blood is fitted and mounted on the narrow diameter part 22 for use.

Accordingly, at the time of collection, the blood is introduced into the outer cylinder 2 from the inner side of the narrow diameter part 22, that is, from the blood inlet opening 23.

Moreover, a plate-like flange 24 is formed integrally on the base end outer periphery of the outer cylinder 2. The operation of moving a plunger 4 relatively with respect to the outer cylinder 2 can be executed with fingers placed on the flange 24.

A gasket 3 made of an elastic material is stored in the outer cylinder 2. The gasket 3 can be slid in the outer cylinder 2 in the longitudinal direction of the outer cylinder 2. At the time, the outer periphery part 31 of the gasket 3 can be slid while closely contacting with the inner peripheral surface 25 of the outer cylinder 2 for providing the fluid-tight property.

The material for the gasket 3 is not particularly limited. Examples thereof include various kinds of rubber materials such as natural rubber, butyl rubber, isoprene rubber, butadiene rubber, styrene-butadiene rubber, silicone rubber, various kinds of thermoplastic elastomers such as polyurethane-based, polyester-based, polyamide-based, olefin-based, and styrene-based, and elastic materials such as a mixture thereof.

A ventilation hole 32 is formed in the center part of the gasket 3 through the base end to the tip end.

A filter member 35 is provided in the vicinity of the tip end of the hole 32 so as to seal the hole 32. The filter member 35 allows permeation of a gas but prevents permeation of a liquid.

Examples of the material for the filter member 35 include various kinds of sintered porous materials, hydrophobic non-woven fabrics, and other kinds of porous materials. In this case, as the sintered porous materials, those obtained by sintering a material containing a polymer material (powdery) such as a polyethylene and a hydrophilic (water-soluble, water-swellable) polymer are preferable.

The plunger 4 for the moving operation of the gasket 3 is interlocked with the base end side of the gasket 3.

The plunger 4 comprises a substantially cylindrical member, with a mushroom-like head part 41 formed on the tip end part thereof. The head part 41 is inserted into the hole 32 from the base end side of the gasket 3 so as to be engaged with an engaging part 33 formed on the base end of the gasket 3. Accordingly, in the case where the plunger 4 is moved to the base end direction or to the tip end direction, the gasket 3 follows the movement.

Moreover, a ventilation hole 42 is formed in the head part 41, communicating with the hole 32 of the gasket 3 and the internal space 43 of the plunger 4.

The internal space 43 of the plunger 4 is opened to the base end of the plunger 4. Moreover, a ring-like flange 44 is formed integrally on the base end part outer periphery of the plunger 4. The operation of moving the plunger 4 relatively with respect to the outer cylinder 2 can be executed with fingers placed on the flange 44.

Examples of the material for the outer cylinder 2 and the plunger 4 include polyesters and butadiene-styrene copolymers, such as polyvinyl chloride, polyethylene, polypropylene, polystyrene, poly-(4-methyl pentene-1), polycarbonate, acrylic resin, acrylnitrile-butadiene-styrene copolymer, and polyethylene terephthalate, and various kinds of resins such as polyamide (for example, nylon 6, nylon 6•6, nylon 6•10, nylon 12). Among these examples, resins such as polypropylene, polyester, and poly-(4-methyl pentene-1) are preferable for the shaping easiness.

It is preferable that the material of the outer cylinder 2 is substantially transparent for ensuring the visibility of the inside.

In the blood-collecting device 1, an anti-coagulation agent supply piece 5 is stored in the space 26 surrounded by the outer cylinder 2 and the gasket 3. The anti-coagulation agent supply piece 5 serves for supplying an anti-coagulation agent supported thereon to the blood introduced into the outer cylinder 2. Hereafter, the configuration of the anti-coagulation agent supply piece 5 will be explained.

As shown in FIG. 2, the anti-coagulation agent supply piece 5 comprises a plate-like supporting member 51, with an anti-coagulation agent 52 supported on both surfaces thereof. Unlike the embodiment shown in the figure, the anti-coagulation agent 52 may be supported only on one side of the supporting member 51.

The material for the supporting member 51 is not particularly limited, but a material insoluble with a liquid such as the blood is preferable. Accordingly, elution of the supporting member material into the collected blood so as to affect the analysis and the measurement can be prevented.

Moreover, as the material for the supporting member 51, porous materials such as a membrane filter, woven fabric, non-woven fabric, and a porous resin film can be used, but a non-porous material is preferable. In the case where the supporting member 51 is made of a non-porous material, the mixing property of the anti-coagulation agent 52 with respect to the blood is improved as well as generation of bubbles at the time of introducing the blood and thereafter can certainly be restrained.

Examples of the non-porous material include films of various kinds of resins such as polyesters including polyethylene, polypropylene, ionomer, and polyethylene terephthalate, polystyrene, poly-(4-methyl pentene-1), polyamide, acrylic resins, and polyvinyl chloride.

The thickness of the supporting member 51 is not particularly limited, but in the case where the supporting member 51 is made of a non-porous material, about 0.025 to 2.0 mm thickness is preferable, and about 0.03 to 0.1 mm thickness is more preferable.

The surface (the surface in contact with the anti-coagulation agent 52) 53 of the supporting member 51 can be flat as shown in FIG. 2, but one with minute ruggedness 54 formed as shown in FIG. 3 is preferable. Accordingly, the anti-coagulation agent 52 layer can be formed easily as well as the adhesion property of the anti-coagulation agent 52 can be improved, and thus it is advantageous.

As the size of the minute ruggedness 54, a surface coarseness Ra of the surface 53 of 5 to 100 μm, in particular, 5 to 30 μm can be presented.

The method for forming the minute ruggedness 54 is not particularly limited, and examples thereof include an emboss process, a satin process, and shot blast (for example, collision of silica particles).

Examples of the anti-coagulation agent 52 include heparin (sodium chloride+sodium heparin), ACD liquid (sodium citrate, citric acid, grape sugar), CPD liquid (sodium citrate, citric acid, grape sugar, sodium monophosphate), CPD-1 liquid (sodium citrate, citric acid, grape sugar, sodium monophosphate, adenine), urokinase, TPA, EDTA•2Na, and EDTA•3K. Hereafter, the case of the heparin will be explained as the representative thereof.

The method for supporting the anti-coagulation agent 52 on the supporting member 51 is not particularly limited, and a so-called application method, such as a method of soaking (applying) the supporting member 51 in an aqueous solution of an anti-coagulation agent and drying, and a method of applying an aqueous solution of an anti-coagulation agent on the surface 53 of the supporting member 51 by spray, a roller, or a blush, and drying can be presented. In this case, the drying method includes air-drying with cold air or hot air, and heat-drying by an oven. That is, the drying operation is executed preferably at an ordinary temperature or higher.

According to the method mentioned above, a desired supporting amount of the anti-coagulation agent 52 can be supported on the supporting member 51 easily and certainly.

In particular, in the case of supporting a low unit (for example, about 7 unit) of the heparin (anti-coagulation agent), the following advantages can be provided.

In the conventional embodiment by freeze-drying, in the case of a low unit heparin, an extending agent such as polyvinyl pyrrolidone (PVP) should be added. However, in the invention, even in the case of supporting a low unit heparin, addition of the extending agent is unnecessary, and by adjusting the heparin concentration in the aqueous solution (soaking liquid, application liquid) of the heparin and the application area, the low unit heparin can be supported easily as well as the supporting amount thereof can be identified accurately.

Moreover, unlike the conventional embodiment by the freeze-drying, the anti-coagulation agent 52 does not involve the risk of the deliquescence by moisture absorption. Therefore, the solubility and mixing property with respect to the blood can be maintained preferably. Furthermore, there is no need of wrapping the entire blood-collecting device with a special wrapping material with the excellent vapor barrier property, such as a wrapping material comprising a laminated film having an aluminum thin layer for preventing the moisture. Therefore, the visibility of the inside of the wrapping material can be ensured and thus it is advantageous in terms of the quality control as well as the cost on the wrapping material can be cut back and the disposal process of the wrapping material can be facilitated. As the wrapping material, a transparent plastic film conventionally used for the medical devices can be adopted. For example, a PET/PE laminated film is preferable. As the sterilization method, a γ ray sterilization, and an electron beam sterilization are preferable.

Furthermore, compared with the conventional embodiment by the freeze-drying, according to the layer-like anti-coagulation agent 52 of this embodiment, bubble generation can be reduced at the time of introducing the blood.

The shape and the arrangement of the anti-coagulation agent supply piece 5 will be explained.

The tip end side 50 of the anti-coagulation agent supply piece 5 has a shape tapered toward the blood inlet opening 22. The tip end (corner part 57) of the tapered shape may be round (R application) to some extent, but it is preferable to be pointed. Accordingly, the effect of preventing bubble generation can further be improved at the time of introducing the blood.

As the anti-coagulation agent supply piece 5 capable of satisfying the conditions, the anti-coagulation agent supply piece 5 according to this embodiment has a hexagonal (in particular, a hexagon symmetrical in the right and left sides with respect to the axis of the outer cylinder 2) shape as shown in FIG. 1. Furthermore, in consideration of the advantages in the production and assembly, a regular hexagon is preferable.

The anti-coagulation agent supply piece 5 is disposed in the direction substantially parallel with the longitudinal direction of the outer cylinder 2. Accordingly, the blood introduced into the outer cylinder 2 via the blood inlet opening 23 can smoothly flow along both surfaces of the anti-coagulation agent supply piece 5 (surface of the anti-coagulation agent 52) so that the anti-coagulation agent 52 can be dissolved and mixed in the blood efficiently.

The anti-coagulation agent supply piece 5 has a pair of sides (rim parts) 55, 56 facing with each other on the right and left sides in FIG. 1. The distance between the sides 55, 56 is same as or more than the inner diameter of the outer cylinder 2. The anti-coagulation agent supply piece 5 maintains its posture by linear contact (contacting linearly) of each of the sides 55, 56 with the inner peripheral surface 25 of the outer cylinder 2.

Figure 8:
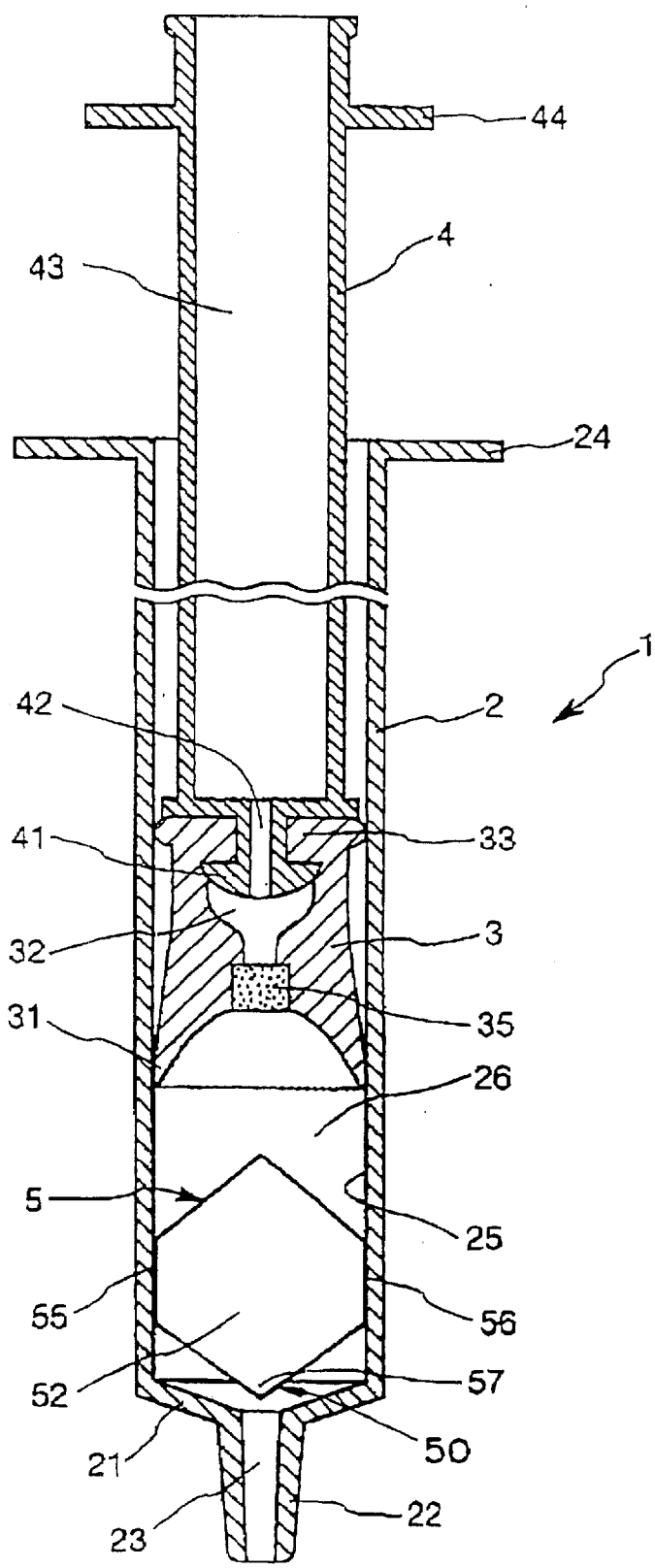
FIG. 8 is a vertical cross-sectional view of another embodiment of a blood-collecting device according to the invention.

Furthermore, it is preferable that the corner part 57 at the tip end of the anti-coagulation agent supply piece 5 is disposed in the blood inlet opening 23 of the narrow diameter part 22 or on the extension toward the direction of the base end of the blood inlet opening 23 (see FIG. 8). In the embodiment shown in FIG. 1, the corner part 57 is disposed in the blood inlet opening 23 of the narrow diameter part 22. In contrast, in the embodiment shown in FIG. 8, the corner part 57 at the tip end of the anti-coagulation agent supply piece 5 is disposed on the extension toward the direction of the base end of the blood inlet opening 23 of the narrow diameter part 22. That is, the corner part 57 is disposed at a position in the vicinity of the center of the outer cylinder 2, away from the base end of the blood inlet opening 23 by a predetermined distance.

According to the arrangement, the anti-coagulation agent supply piece 5 can be supported and fixed on the outer cylinder 2 further stably as well as at the time of introducing the blood from the blood inlet opening 23 into the outer cylinder 2, the effect of restraining deformation of the anti-coagulation agent supply piece 5 can be high, and the certainty in disposing the corner part 57 at an appropriate position can be high. Furthermore, it also contributes to prevent or restrain generation of bubbles effectively at the time of introducing the blood as well as to dissolve or mix the anti-coagulation agent 52 into the blood smoothly. In the embodiment shown in FIG. 8, the corner part 57 of the anti-coagulation agent supply piece 5 can be positioned at an appropriate position further certainly.

The position of the corner part 57 in the outer cylinder longitudinal direction is not limited to the embodiments shown in the figures.

As shown in FIG. 4, the anti-coagulation agent supply piece 5 is disposed in a substantially flat shape (in a straight line) in this embodiment.

Figure 5:
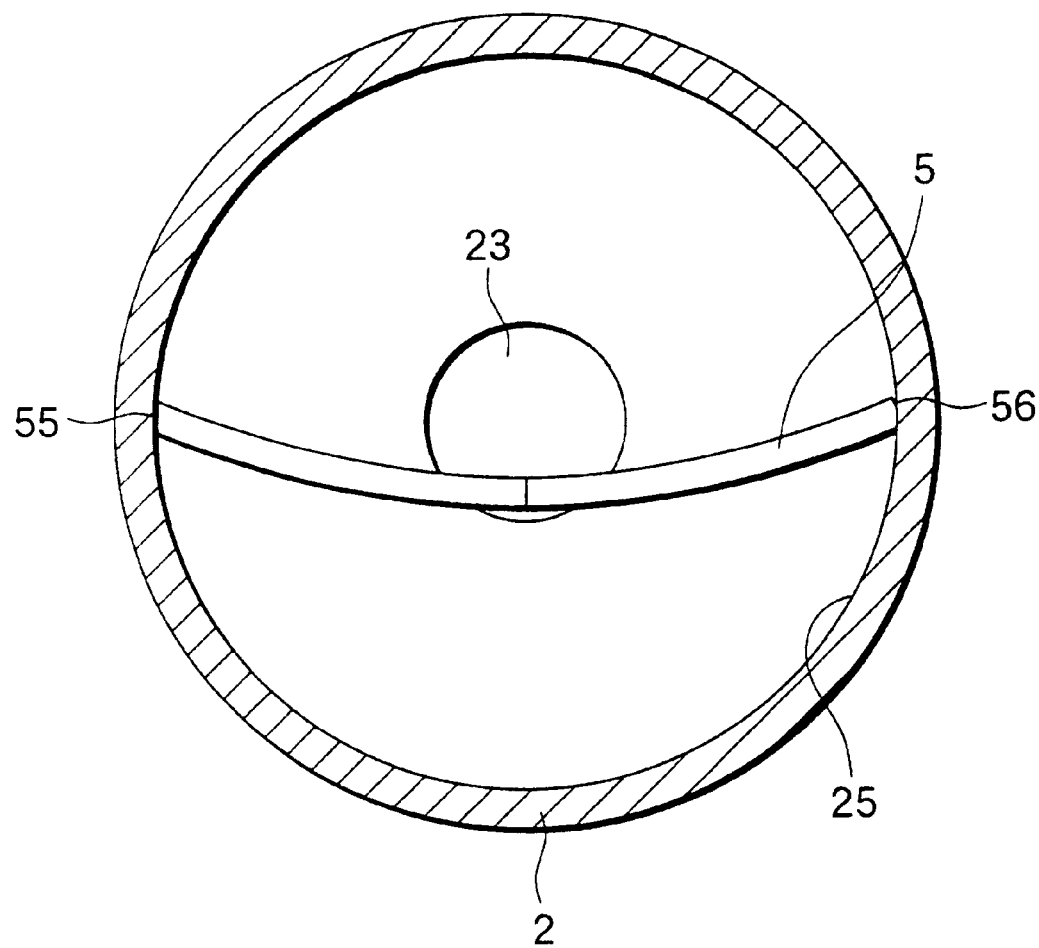
FIG. 5 is a diagram (cross-sectional view taken on the lateral line) showing the posture of the anti-coagulation agent supply piece in an outer cylinder.

Moreover, as shown in FIG. 5, the anti-coagulation agent supply piece 5 can be disposed in the state curved like an arc. Also in this case, it is preferable that the corner part 57 at the tip end of the anti-coagulation agent supply piece 5 is disposed in the blood inlet opening 23 of the narrow diameter part 22 or on the extension toward the direction of the base end of the blood inlet opening 23.

Figure 6:
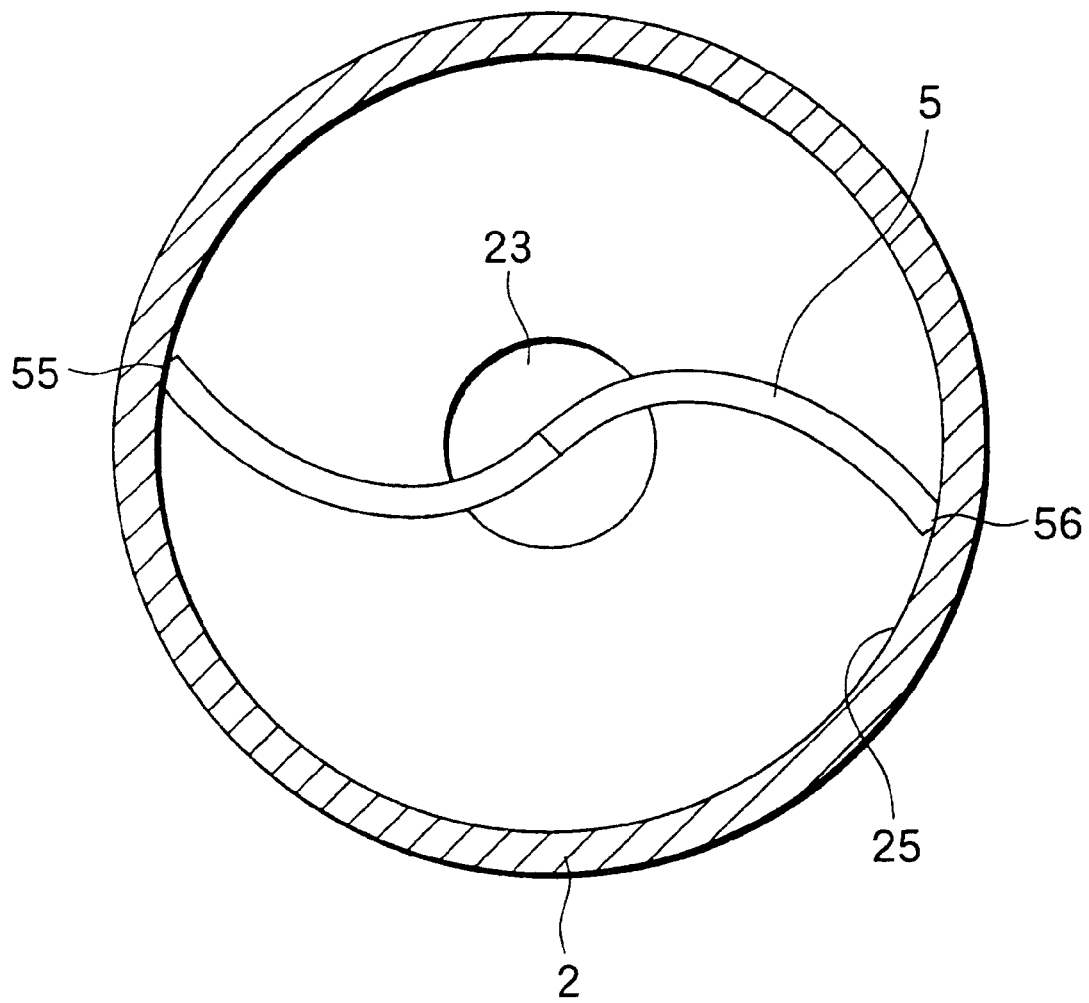
FIG. 6 is a diagram (cross-sectional view taken on the lateral line) showing the posture of the anti-coagulation agent supply piece in an outer cylinder.

Moreover, as shown in FIG. 6, the anti-coagulation agent supply piece 5 can be disposed in the state curved in an S-shape. Also in this case, it is preferable that the corner part 57 at the tip end of the anti-coagulation agent supply piece 5 is disposed in the blood inlet opening 23 or on the extension toward the direction of the base end of the blood inlet opening 23.

Needless to say, the shape and the arrangement of the anti-coagulation agent supply piece 5 according to the invention are not limited to those shown in the figures.

Figure 7:
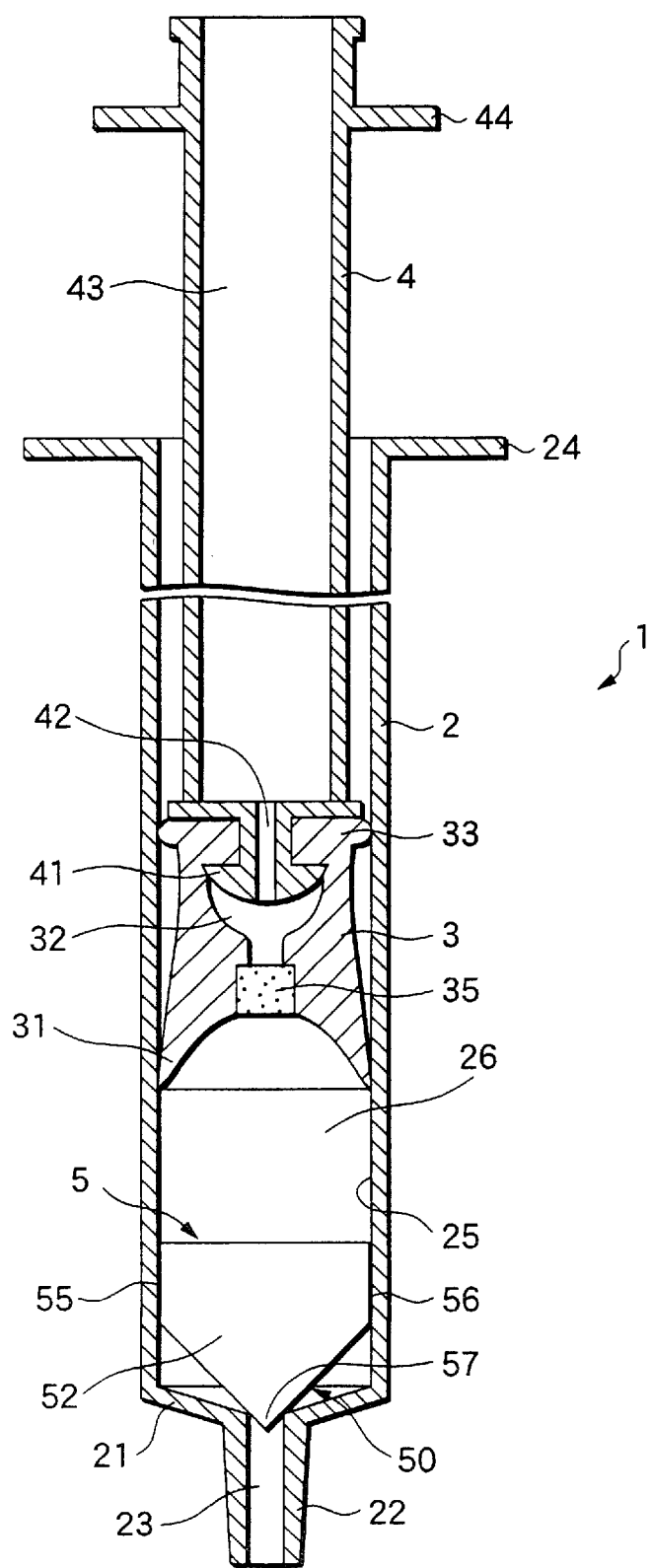
FIG. 7 is a vertical cross-sectional view of another embodiment of a blood-collecting device according to the invention.

For example, as shown in FIG. 7, the anti-coagulation agent supply piece 5 may be pentagonal (home base shape). As other examples of the shape of the anti-coagulation agent supply piece 5, any shape can be adopted such as a triangle, a quadrilateral, a pentagon, an octagon, a circle, an ellipse, an oval, a cannonball shape, and a gourd shape.

As mentioned above, the corner part 57 at the tip end of the anti-coagulation agent supply piece 5 may be disposed on the extension toward the direction of the base end of the blood inlet opening 23 of the narrow diameter part 22. For example, in the embodiment shown in FIG. 8, the tip end of the corner part 57 of the anti-coagulation agent supply piece 5 is at a position in the vicinity of the center of the outer cylinder 2, away from the base end of the blood inlet opening 23 by a predetermined distance. The clearance can be about 0 to 35 mm, in particular, about 0 to 20 mm.

Although the sides (rim parts) of the anti-coagulation agent supply piece 5 at the tip end side 50 are of straight lines (tapered state) in FIGS. 1, 7 and 8, the sides may be curved.

An embodiment of a production method for the anti-coagulation agent supply piece 5 will be explained.

First, a large supporting member sheet (not illustrated) is prepared, and a layer of the anti-coagulation agent 52 is formed on one side or both sides thereof by the method explained above.

Next, the supporting member sheet is cut or punched into a desired shape (for example, the hexagon as shown in the figure or in a pentagon). Accordingly, the anti-coagulation agent supply piece 5 can be obtained. The anti-coagulation agent supply piece 5 is mounted at a predetermined position in the outer cylinder 2 as mentioned above. Since a large number of the anti-coagulation agent supply pieces 5 can be obtained from one supporting member sheet, the production efficiency is extremely high. Moreover, the operativity at the time of mounting the obtained anti-coagulation agent supply piece 5 into the outer cylinder 2 is good.

Next, an embodiment of the method of using the blood-collecting device 1 will be explained.

With a blood-collecting needle (not illustrated) mounted on the narrow diameter part 22 of the outer cylinder 2, the blood-collecting needle is stuck into the artery. Then, according to the blood pressure in the artery, the blood flows to the base end direction through the inside of the blood-collecting needle and the blood inlet opening 23 of the narrow diameter part 22 so as to be introduced into the outer cylinder 2 (the space 26 surrounded by the outer cylinder 2 and the gasket 3).

The blood flowing through the blood inlet opening 23 toward the base end direction first contacts with the corner part 57 of the anti-coagulation agent supply piece 5, and spreads gradually therefrom so as to flow along the surface of the anti-coagulation agent 52 and gradually fill the space 26. Accordingly, the anti-coagulation agent 52 is dissolved and mixed in the blood. At the time, since the blood flows along the surface of the anti-coagulation agent supply piece 5 smoothly, bubbles can hardly be generated. That is, the bubble generation can be prevented or restrained at the time of introducing the blood into the space 26.

Moreover, according to the influx of the blood into the space 26, the air in the space 26 permeates the filter member 35 so as to be discharged to the outside via the holes 32, 42 and the internal space 43, successively. Accordingly, the blood can be introduced smoothly into the space 26.

In the case where the space 26 is filled with the blood, the filter member 35 comes in contact with the blood so as to be wetted by the blood. According to the function of blocking the blood permeation by the filter member 35, the leakage of the blood can be prevented.

When the space 26 is filled up with the blood, the blood-collecting needle is pulled out from the artery and covered with a cap for protection. Thereafter, the blood-collecting device 1 is swayed, vibrated, rotated, or turned around vertically for facilitating dissolution and mixture of the anti-coagulation agent 52 with the blood.

Since an appropriate amount of the anti-coagulation agent 52 is dissolved and mixed in the blood in the space 26 sufficiently, an optimum anti-coagulation effect can be provided.

The blood collected in the blood-collecting device 1 as mentioned above is provided for analysis and examination. As mentioned above, since the bubble generation is prevented or restrained at the time of introducing the blood into the space 26, a further accurate measurement value can be obtained in measuring the gas partial pressure in the collected blood.

In the case of taking out the collected blood in the blood-collecting device 1, the plunger 4 is pressured and moved to the tip end direction for reducing the volume of the space 26 so as to discharge the blood from the tip end of the narrow diameter part 22.

At the time, since the filter member 35 wetted by the blood does not allow permeation of the blood, the blood cannot flow backward to the base end direction through the hole 32 so as to be leaked.

The invention is not limited to the arterial blood-collecting devices explained above, but it can be adopted for a venous blood-collecting device as well.

Next, specific embodiments of the invention will be explained.

EXAMPLE 1

A blood-collecting device (for collecting the arterial blood) was produced with the configuration shown in FIGS. 1, 3 and 4. The specification of the arterial blood-collecting device is as follows.
1. Outer cylinder
   Outer cylinder material: polypropylene
   Inner diameter: 9.0 mm
   Volume of the space 26: 2.5 ml
2. Plunger
   Plunger material: polypropylene
3. Gasket
   Gasket material: silicone rubber
   Filter member: polyethylene sintered porous material (containing a starch acrylic based highly absorbent polymer)
4. Anti-coagulation agent supply piece
   Shape: regular hexagon
   Size: 9.0 mm distance between the sides 55, 56
   Supporting member material: polyethylene terephthalate
   Supporting member thickness: 0.075 mm
   Supporting member surface area: 1.4 cm$^2$ for the total of the front and back sides
   Surface state of the supporting member: minute ruggedness formed on the entire surface (surface coarseness Ra=15 $\mu$m)
   Anti-coagulation agent: heparin (two kinds of supporting amounts: 7 unit and 125 unit)
   Part of supporting the anti-coagulation agent: entire surfaces on both sides of the supporting member
   Method of supporting the anti-coagulation agent: By soaking supporting members in aqueous solutions of a heparin each with the heparin concentration adjusted so as to provide a 7 unit or 125 unit supporting amount after drying, and drying with a 110° C. hot air, heparin layers were formed with about 3 $\mu$m average thickness (7 unit) or with about 30 $\mu$m average thickness (125 unit).
   Position of the tip end of the corner part 57 of the anti-coagulation agent supply piece: inside of the blood inlet opening 23

The arterial blood-collecting device was stored and sealed in a wrapping material made of a PET/PE laminated film so as to be left for 60 days in a 30° C., 80% RH environment. The heparin in the outer cylinder 2 was in the normal state without degeneration.

EXAMPLE 2

In the same process as in the Example 1 except that the position of the anti-coagulation agent supply piece in the outer cylinder is changed to the position shown in FIG. 8 (the tip end of the corner part 57 of the anti-coagulation agent supply piece is at a position away from the base end of the blood inlet opening 23 by about 3 mm), an arterial blood-collecting device was produced. The arterial blood-collecting device was stored and sealed in the same wrapping material made of a PET/PE laminated film so as to be left for 60 days in a 30° C., 80% RH environment. The heparin in the outer cylinder 2 was in the normal state without degeneration.

EXAMPLE 3

In the same process as in the Example 1, a blood-collecting device (for collecting the arterial blood) was produced with the configuration shown in FIGS. 1, 3 and 4. The specification of the arterial blood-collecting device of the Example 3 is same as that of the Example 1 except for the specification of the anti-coagulation agent supply piece shown below.
*Anti-coagulation agent supply piece
   Shape: regular hexagon
   Supporting member material: polyethylene terephthalate
   Supporting member thickness: 0.075 mm
   Supporting member surface area: 1.4 cm$^2$ for the total of the front and back sides
   Surface state of the supporting member: minute ruggedness formed on the entire surface (surface coarseness Ra=15 $\mu$M)

Anti-coagulation agent: heparin (two kinds of supporting amounts: 7 unit and 125 unit)

Part of supporting the anti-coagulation agent: entire surfaces on both sides of the supporting member Method of supporting the anti-coagulation agent: By soaking supporting members in aqueous solutions of a heparin each with the heparin concentration adjusted so as to provide a 7 unit or 125 unit supporting amount after drying, and drying with a 110° C. hot air, heparin layers were formed with about 3 μm average thickness (7 unit) or with about 30 μm average thickness (125 unit).

Position of the tip end of the corner part 57 of the anti-coagulation agent supply piece: at a position away from the base end of the internal space (blood inlet opening) 23 by about 3 mm The arterial blood-collecting device was stored and sealed in a wrapping material made of a PET/PE laminated film so as to be left for 60 days in a 30° C., 80% RH environment. The heparin in the outer cylinder 2 was in the normal state without degeneration.

COMPARATIVE EXAMPLE 1

Figure 9:
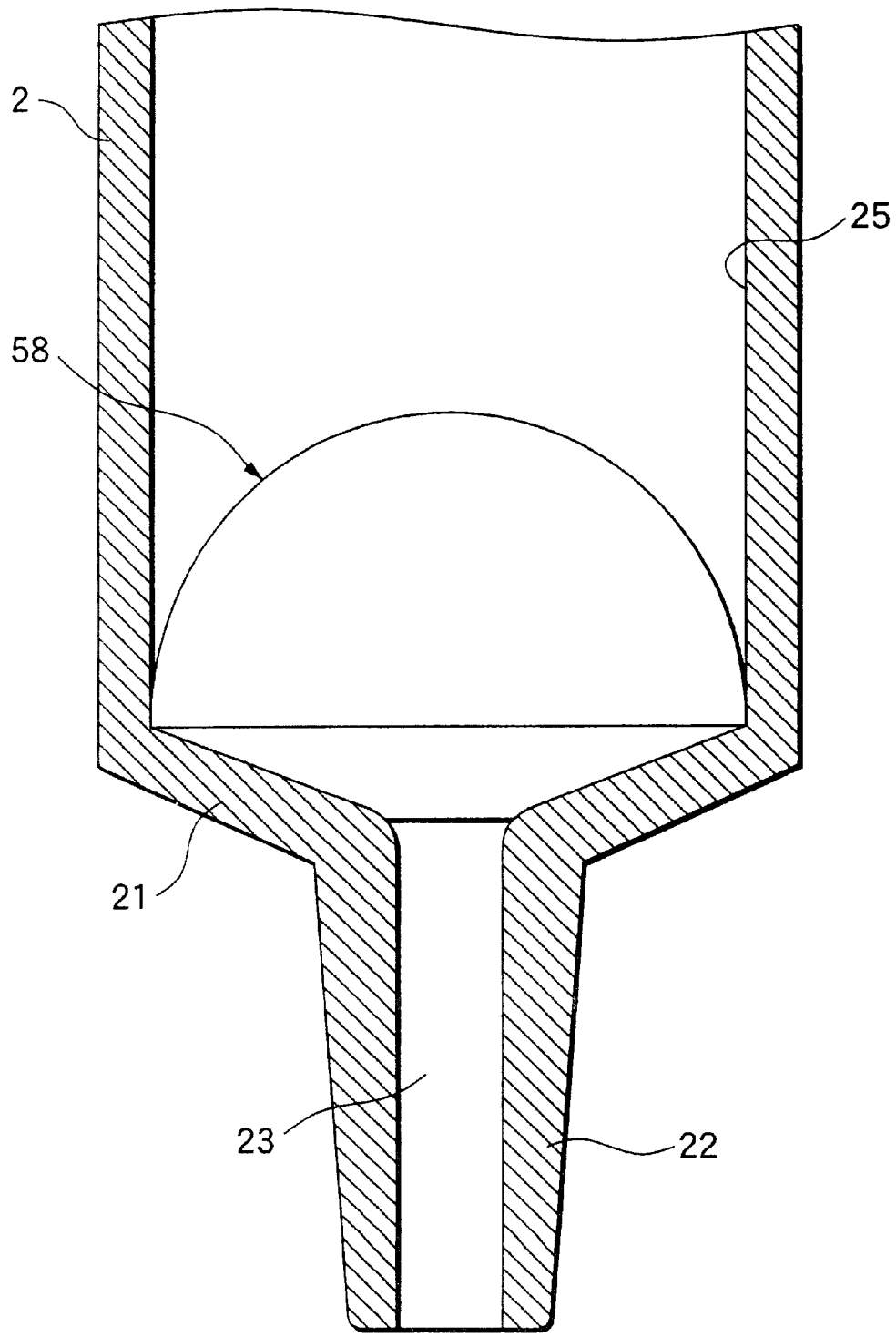
FIG. 9 is a vertical cross-sectional view showing the shape and the posture of an anti-coagulation agent supply piece in a blood-collecting device of a Comparative Example.

In the same process as in the Example 1 except that an anti-coagulation agent supply piece 58 cut in a semi-circular shape and disposed at a position as shown in FIG. 9 was used, an arterial blood-collecting device was produced. The arterial blood-collecting device was stored and sealed in the same wrapping material made of a PET/PE laminated film as in the Example 3 so as to be left for 60 days in a 30° C., 80% RH environment.

COMPARATIVE EXAMPLE 2

In the same process as in the Example 1 except that a heparin (two kinds: 7 unit and 125 unit) was provided by dropping an aqueous solution of a heparin with a desired concentration (with PVP added by 0.3% for 7 unit) into the outer cylinder 2, and freeze-drying at −20° C., an arterial blood-collecting device was produced.

The arterial blood-collecting device was stored and sealed in a wrapping material with a vapor barrier property (comprising a three layer laminated sheet including a PET film/an aluminum thin layer/a PE film) so as to be left for 60 days in a 30° C., 80% RH environment. The heparin in the outer cylinder 2 hardly absorbed the moisture and in the substantially normal state.

COMPARATIVE EXAMPLE 3

The same arterial blood-collecting device as in the Comparative Example 2 was stored and sealed in the same wrapping material made of a PET/PE laminated film as in the Example 1 so as to be left for 60 days in a 30° C., 80% RH environment. The heparin in the outer cylinder 2 was liquidized due to the deliquescence phenomenon generated by the moisture absorption.

COMPARATIVE EXAMPLE 4

An arterial blood-collecting device produced in the same process as in the Comparative Example 3 except that the anti-coagulation agent supply piece was not provided was stored and sealed in the same wrapping material made of a PET/PE laminated film as in the Example 3 so as to be left for 60 days in a 30° C., 80% RH environment.

<Experiment 1>

The arterial blood-collecting devices of the Examples 1, 2 and the Comparative Examples 1, 2 were taken out from the wrapping materials. The arterial blood of a human was collected with the arterial blood-collecting devices (No. 1 to 10).

Whether or not bubbles are generated in the outer cylinder was observed visibly. Results are shown in Table 1.

Meaning of the marks in Table 1 are as follows:

○: without bubble generation

×: with bubble generation

TABLE 1

State of the bubble generation

| | Heparin 7 unit | | | | Heparin 125 unit | | | |
| --- | --- | --- | --- | --- | --- | --- | --- | --- |
| No. | Example 1 | Example 2 | Comparative Example 1 | Comparative Example 2 | Example 1 | Example 2 | Comparative Example 1 | Comparative Example 2 |
| 1 | ○ | ○ | ○ | ○ | ○ | ○ | X | ○ |
| 2 | ○ | ○ | X | ○ | ○ | ○ | ○ | X |
| 3 | ○ | ○ | X | ○ | ○ | ○ | ○ | ○ |
| 4 | ○ | ○ | ○ | X | ○ | ○ | X | ○ |
| 5 | ○ | ○ | X | ○ | ○ | ○ | X | ○ |
| 6 | ○ | ○ | ○ | ○ | ○ | ○ | X | X |
| 7 | ○ | ○ | X | ○ | ○ | ○ | ○ | ○ |
| 8 | ○ | ○ | ○ | ○ | ○ | ○ | ○ | ○ |
| 9 | ○ | ○ | X | X | ○ | ○ | ○ | ○ |
| 10 | ○ | ○ | X | ○ | ○ | ○ | X | ○ |

<Experiment 2>

The arterial blood-collecting devices of the Examples 1, 2 and the Comparative Examples 1, 2 were taken out from the wrapping materials. The arterial blood of a human was collected with the arterial blood-collecting devices (No. 11 to 20).

After the collection, the collected blood was agitated by rotating the blood-collecting devices in the right and left direction for 10 times. After leaving for 15 minutes (No. 11 to 15) and for 30 minutes (No. 16 to 20), whether or not the blood coagulation is generated in the collected blood was judged.

The judgment was made by discharging the collected blood onto a filter paper, adding a physiological saline while suctioning the blood, visibly observing the degree of the blood coagulation lump (clot) existing on the filter paper, and classifying the degree into the following 4 grades. Judgment results are shown in Table 2.

⊚: no blood coagulation lump at all

○: slight blood coagulation lumps

Δ: with blood coagulation lumps

×: with a large number of blood coagulation lumps, or the entirety set in a jelly-like state

TABLE 2

Solubility and mixing property of the heparin

| | Left | Heparin 7 unit | | | | Heparin 125 unit | | | |
| --- | --- | --- | --- | --- | --- | --- | --- | --- | --- |
| No. | Time (min.) | Example 1 | Example 2 | Comparative Example 1 | Comparative Example 2 | Example 1 | Example 2 | Comparative Example 1 | Comparative Example 2 |
| 11 | 15 | ⊚ | ⊚ | ○ | Δ | ⊚ | ⊚ | ○ | ○ |
| 12 | 15 | ⊚ | ⊚ | ○ | ○ | ⊚ | ⊚ | ○ | ○ |
| 13 | 15 | ⊚ | ⊚ | ○ | Δ | ⊚ | ⊚ | ⊚ | ○ |
| 14 | 15 | ⊚ | ⊚ | ○ | Δ | ⊚ | ⊚ | ○ | ○ |
| 15 | 15 | ⊚ | ⊚ | ○ | Δ | ⊚ | ⊚ | ⊚ | ○ |
| 16 | 30 | ⊚ | ⊚ | ○ | X | ⊚ | ⊚ | ○ | Δ |
| 17 | 30 | ○ | ⊚ | Δ | Δ | ⊚ | ⊚ | ○ | ○ |
| 18 | 30 | ⊚ | ○ | ○ | X | ⊚ | ⊚ | ○ | ○ |
| 19 | 30 | ⊚ | ⊚ | ○ | X | ⊚ | ⊚ | ○ | ○ |
| 20 | 30 | ⊚ | ○ | Δ | Δ | ⊚ | ⊚ | ○ | Δ |

<Evaluation of the Experiment 1 and Experiment 2>

As shown in Tables 1 and 2, in the blood-collecting device according to the Examples 1, 2 of the invention, bubbles are not generated at the time of collecting the blood, the deliquescence phenomenon of the heparin is not generated even though it is wrapped with an ordinary wrapping material, and the excellent anti-coagulation effect is provided continuously owing to sufficient dissolution and mixture to the blood. In particular, even in the case with a low unit (7 unit) of a heparin supported, the excellent anti-coagulation effect is provided.

In contrast, in the blood-collecting device of the Comparative Examples 1, 2, bubbles are generated at the time of collecting the blood so that the bubbles are mixed in the collected blood. Moreover, although the deliquescence phenomenon of the heparin is prevented in the blood-collecting device of the Comparative Example 2 because it is wrapped with a special expensive material with the vapor barrier property, the dissolving property and the mixing property to the blood are poorer than those of the Examples 1, 2.

Since the arterial blood-collecting device of the Comparative Example 3 is wrapped with an ordinary wrapping material with a poor vapor barrier property, the heparin is liquidized due to the deliquescence phenomenon generated by the moisture absorption. Therefore, the existence of the heparin cannot be observed. Furthermore, due to adhesion of the liquidized heparin onto the filter member so as to cause choking, the product value is lost.

<Experiment 3>

The arterial blood-collecting devices of the Example 3 and the Comparative Examples 2, 4 were taken out from the wrapping materials. The arterial blood of a human was collected with the arterial blood-collecting devices (each 40 pieces).

Immediately after the collection, the collected blood was agitated by rotating the blood-collecting devices in the right and left direction for predetermined times. The number of rotations varied in 4 stages including 0, 5, 10 and 20 times. 10 each pieces were used for each number of rotations. Immediately after the operation, whether or not the blood coagulation is generated in the collected blood was judged.

The judgment was made by discharging the collected blood onto a filter paper, adding a physiological saline while suctioning the blood, and visibly observing whether or not the blood coagulation lump (clot) exists on the filter paper. In the case where even one piece of the blood lump is found, it is judged that the blood coagulation exists. Judgment results (number of those having the blood coagulation) are shown in Table 3.

TABLE 3

Immediately after the blood introduction

| | Without supply of an anti-coagulation agent supply piece Comparative Example 4 | Heparin 7 unit | | Heparin 125 unit | |
| --- | --- | --- | --- | --- | --- |
| Number of rotations | | Anti-coagulation agent supply piece Comparative Example 3 | Freeze-drying Comparative Example 2 | Anti-coagulation agent supply piece Comparative Example 3 | Freeze-drying Comparative Example 2 |
| 0 time | 0/10 | 0/10 | 0/10 | 0/10 | 0/10 |
| 5 times | 0/10 | 0/10 | 0/10 | 0/10 | 0/10 |
| 10 times | 0/10 | 0/10 | 0/10 | 0/10 | 0/10 |
| 20 times | 0/10 | 0/10 | 0/10 | 0/10 | 0/10 |

After passage of 10 minutes from the previous judgment, whether or not the blood coagulation is generated in the collected blood was judged again in the same manner. Judgment results are shown in Table 2.

TABLE 4

After passage of 10 minutes

| Number of rotations | Without supply of an anti-coagulation agent supply piece Comparative Example 4 | Heparin 7 unit | | Heparin 125 unit | |
|---|---|---|---|---|---|
| | | Anti-coagulation agent supply piece Comparative Example 3 | Freeze-drying Example 2 | Anti-coagulation agent supply piece Comparative Example 3 | Freeze-drying Comparative Example 2 |
| 0 time | 10/10 | 0/10 | 0/10 | 0/10 | 0/10 |
| 5 times | 10/10 | 0/10 | 0/10 | 0/10 | 0/10 |
| 10 times | 10/10 | 0/10 | 0/10 | 0/10 | 0/10 |
| 20 times | 10/10 | 0/10 | 0/10 | 0/10 | 0/10 |

After passage of 20 minutes from the initial judgment, whether or not the blood coagulation is generated in the collected blood was judged again in the same manner. Judgment results are shown in Table 5.

TABLE 5

After passage of 20 minutes

| Number of rotations | Without supply of an anti-coagulation agent supply piece Comparative Example 4 | Heparin 7 unit | | Heparin 125 unit | |
|---|---|---|---|---|---|
| | | Anti-coagulation agent supply piece Comparative Example 3 | Freeze-drying Example 2 | Anti-coagulation agent supply piece Comparative Example 3 | Freeze-drying Comparative Example 2 |
| 0 time | 10/10 | 1/10 | 6/10 | 0/10 | 1/10 |
| 5 times | 10/10 | 0/10 | 4/10 | 0/10 | 0/10 |
| 10 times | 10/10 | 0/10 | 2/10 | 0/10 | 0/10 |
| 20 times | 10/10 | 0/10 | 0/10 | 0/10 | 0/10 |

<Evaluation of the Experiment 3>

As shown in Tables 3 to 5, in the blood-collecting device according to the invention, the deliquescence phenomenon of the heparin is not generated even though it is wrapped with an ordinary wrapping material, and the excellent anti-coagulation effect is provided continuously owing to sufficient dissolution and mixture to the blood. In particular, even in the case with a low unit (7 unit) of a heparin supported, the excellent anti-coagulation effect is provided.

In contrast, in the blood-collecting device of the Comparative Example 2, although the deliquescence phenomenon of the heparin is prevented because it is wrapped with a special expensive material with the vapor barrier property, the dissolving property and the mixing property to the blood are poorer than the case of the Examples of the invention.

In contrast, since the arterial blood-collecting device of the Comparative Example 3 is wrapped with an ordinary wrapping material with a poor vapor barrier property, the heparin is liquidized due to the deliquescence phenomenon generated by the moisture absorption. Therefore, the existence of the heparin cannot be observed. Furthermore, due to adhesion of the liquidized heparin onto the filter member so as to cause choking, the product value is lost.

As heretofore explained, according to a blood-collecting device of the invention, generation of bubbles can be prevented or restrained at the time of collecting the blood (blood collection) so as to prevent the adverse effect derived from the bubbles mixed therein. For example, in the case of analyzing and measuring the dissolved oxygen amount in the arterial blood, a further accurate analysis result can be obtained.

Moreover, according to a blood-collecting device of the invention, the excellent solubility and mixing property of the anti-coagulation agent with respect to the blood and a sufficient anti-coagulation effect can be provided.

Furthermore, since the risk of moisture absorption can be eliminated compared with the conventional embodiment with an anti-coagulation agent freeze-dried, the moisture absorption prevention measure such as wrapping with a special wrapping material with the vapor barrier property can be eliminated or reduced (alleviated), and thus the production cost can be cut back.

Moreover, since an anti-coagulation agent supply piece can be produced easily with a good productivity as well as it can be assembled easily in a blood-collecting device, a blood-collecting device with a good production efficiency can be provided.

What is claimed is:

1. A blood-collecting device comprising:

an outer cylinder including a blood inlet opening;

a gasket slidable in said outer cylinder;

a plunger for moving operation of said gasket;

an anti-coagulation agent supply piece with an anti-coagulation agent supported on at least one side of a plate-shaped supporting member, provided in a space surrounded by the outer cylinder and the gasket; and said anti-coagulation agent supply piece maintaining a posture in the space by contact of a part of said anti-coagulation agent supply piece with an inner surface of the outer cylinder.

2. The blood-collecting device according to claim 1, wherein said anti-coagulation agent supply piece has a shape tapered toward the blood inlet opening.

3. The blood-collecting device according to claim 2, wherein the tip end of the tapered shape of said anti-coagulation agent supply piece is pointed.

4. The blood-collecting device according to claim 1, wherein said anti-coagulation agent supply piece maintains the posture by linear contact of a rim part of said anti-coagulation agent supply piece with the inner surface of the outer cylinder.

5. The blood-collecting device according to claim 2, wherein said anti-coagulation agent supply piece maintains the posture by linear contact of a rim part of said anti-coagulation agent supply piece with the inner surface of the outer cylinder.

6. The blood-collecting device according to claim 1, wherein said anti-coagulation agent supply piece has a polygonal shape.

7. The blood-collecting device according to claim 1, wherein the anti-coagulation agent is supported by applying a solution of the anti-coagulation agent on the surface of the supporting member, and drying at an ordinary temperature or higher.

8. The blood-collecting device according to claim 1, wherein said anti-coagulation agent supply piece is disposed in a direction substantially parallel with the longitudinal direction of the outer cylinder.

9. The blood-collecting device according to claim 1, wherein a ventilation part is formed in said gasket and said plunger.

10. The blood-collecting device according to claim 1, wherein a gas permeable filter member preventing permeation of a liquid is provided in said gasket.

11. The blood-collecting device according to claim 1, wherein the supporting member is made of a material insoluble with respect to blood.

12. The blood-collecting device according to claim 1, wherein minute ruggedness is formed on the surface of the supporting member in contact with the anti-coagulation agent.

13. A medical device comprising a blood-collecting device, said blood-collecting device including:

an outer cylinder including a blood inlet opening;

a gasket slidable in said outer cylinder;

a plunger for moving operation of said gasket;

an anti-coagulation agent supply piece with an anti-coagulation agent supported on at least one side of a plate-shaped supporting member, provided in a space surrounded by the outer cylinder and the gasket;

said anti-coagulation agent supply piece maintaining a posture in the space by contact of a part of said anti-coagulation agent supply piece with an inner surface of the outer cylinder; and wherein said blood-collecting device is wrapped in a plastic film and applied with sterilization.

* * * * *

UNITED STATES PATENT AND TRADEMARK OFFICE
CERTIFICATE OF CORRECTION

PATENT NO. : 6,511,439 B1
DATED : January 28, 2003
INVENTOR(S) : Tabata et al.

Page 1 of 2

It is certified that error appears in the above-identified patent and that said Letters Patent is hereby corrected as shown below:

Column 14,
Table 3, change

TABLE 3

Immediately after the blood introduction

| | Without supply of an anti-coagulation agent supply piece Comparative Example 4 | Heparin 7 unit | | Heparin 125 unit | |
|---|---|---|---|---|---|
| Number of rotations | | Anti-coagulation agent supply piece Comparative Example 3 | Freeze-drying Comparative Example 2 | Anti-coagulation agent supply piece Comparative Example 3 | Freeze-drying Comparative Example 2 |
| 0 time | 0/10 | 0/10 | 0/10 | 0/10 | 0/10 |
| 5 times | 0/10 | 0/10 | 0/10 | 0/10 | 0/10 |
| 10 times | 0/10 | 0/10 | 0/10 | 0/10 | 0/10 |
| 20 times | 0/10 | 0/10 | 0/10 | 0/10 | 0/10 | to

TABLE 3

Immediately after the blood introduction

| | Without supply of an anti-coagulation agent supply piece Comparative Example 4 | Heparin 7 unit | | Heparin 125 unit | |
|---|---|---|---|---|---|
| Number of rotations | | Anti-coagulation agent supply piece Comparative Example 3 | Freeze-drying Comparative Example 2 | Anti-coagulation agent supply piece Comparative Example 3 | Freeze-drying Comparative Example 2 |
| 0 time | 0/10 | 0/10 | 0/10 | 0/10 | 0/10 |
| 5 times | 0/10 | 0/10 | 0/10 | 0/10 | 0/10 |
| 10 times | 0/10 | 0/10 | 0/10 | 0/10 | 0/10 |
| 20 times | 0/10 | 0/10 | 0/10 | 0/10 | 0/10 |

Column 15,
Table 4, change

TABLE 4

Immediately after the blood introduction

| | Without supply of an anti-coagulation agent supply piece Comparative Example 4 | Heparin 7 unit | | Heparin 125 unit | |
|---|---|---|---|---|---|
| Number of rotations | | Anti-coagulation agent supply piece Comparative Example 3 | Freeze-drying Comparative Example 2 | Anti-coagulation agent supply piece Comparative Example 3 | Freeze-drying Comparative Example 2 |
| 0 time | 0/10 | 0/10 | 0/10 | 0/10 | 0/10 |
| 5 times | 0/10 | 0/10 | 0/10 | 0/10 | 0/10 |
| 10 times | 0/10 | 0/10 | 0/10 | 0/10 | 0/10 |
| 20 times | 0/10 | 0/10 | 0/10 | 0/10 | 0/10 | to

TABLE 4

Immediately after the blood introduction

| | Without supply of an anti-coagulation agent supply piece Comparative Example 4 | Heparin 7 unit | | Heparin 125 unit | |
|---|---|---|---|---|---|
| Number of rotations | | Anti-coagulation agent supply piece Comparative Example 3 | Freeze-drying Comparative Example 2 | Anti-coagulation agent supply piece Comparative Example 3 | Freeze-drying Comparative Example 2 |
| 0 time | 0/10 | 0/10 | 0/10 | 0/10 | 0/10 |
| 5 times | 0/10 | 0/10 | 0/10 | 0/10 | 0/10 |
| 10 times | 0/10 | 0/10 | 0/10 | 0/10 | 0/10 |
| 20 times | 0/10 | 0/10 | 0/10 | 0/10 | 0/10 |

UNITED STATES PATENT AND TRADEMARK OFFICE
CERTIFICATE OF CORRECTION

PATENT NO.   : 6,511,439 B1
DATED        : January 28, 2003
INVENTOR(S)  : Tabata et al.

It is certified that error appears in the above-identified patent and that said Letters Patent is hereby corrected as shown below:

Column 15,
Table 5, change

TABLE 5

|  | Immediately after the blood introduction | | | | |
|---|---|---|---|---|---|
|  | Without supply of an anti-coagulation agent supply piece | Heparin 7 unit | | Heparin 125 unit | |
|  |  | Anti-coagulation agent supply piece | Freeze-drying | Anti-coagulation agent supply piece | Freeze-drying |
| Number of rotations | Comparative Example 4 | Comparative Example 3 | Comparative Example 2 | Comparative Example 3 | Comparative Example 2 |
| 0 time | 0/10 | 0/10 | 0/10 | 0/10 | 0/10 |
| 5 times | 0/10 | 0/10 | 0/10 | 0/10 | 0/10 |
| 10 times | 0/10 | 0/10 | 0/10 | 0/10 | 0/10 |
| 20 times | 0/10 | 0/10 | 0/10 | 0/10 | 0/10 | to

TABLE 5

|  | Immediately after the blood introduction | | | | |
|---|---|---|---|---|---|
|  | Without supply of an anti-coagulation agent supply piece | Heparin 7 unit | | Heparin 125 unit | |
|  |  | Anti-coagulation agent supply piece | Freeze-drying | Anti-coagulation agent supply piece | Freeze-drying |
| Number of rotations | Comparative Example 4 | Comparative Example 3 | Comparative Example 2 | Comparative Example 3 | Comparative Example 2 |
| 0 time | 0/10 | 0/10 | 0/10 | 0/10 | 0/10 |
| 5 times | 0/10 | 0/10 | 0/10 | 0/10 | 0/10 |
| 10 times | 0/10 | 0/10 | 0/10 | 0/10 | 0/10 |
| 20 times | 0/10 | 0/10 | 0/10 | 0/10 | 0/10 |

Signed and Sealed this

Twentieth Day of July, 2004

JON W. DUDAS
*Acting Director of the United States Patent and Trademark Office*